US009617281B2

(12) United States Patent
Alcalde-Pais et al.

(10) Patent No.: US 9,617,281 B2
(45) Date of Patent: Apr. 11, 2017

(54) IMIDAZO[2,1-B]THIAZOLE DERIVATIVES, THEIR PREPARATION AND USE AS MEDICAMENTS

(71) Applicant: LABORATORIOS DEL DR. ESTEVE S.A., Barcelona (ES)

(72) Inventors: María de las Ermitas Alcalde-Pais, Sant Just Desvern (ES); José Luís Diaz Fernández, Manresa (ES); María de les Neus Mesquida-Estevez, Sant Esteve Sesrovires (ES); Laura Paloma-Romeu, La Garriga (ES)

(73) Assignee: LABORATORIES DEL DR. ESTEVE S.A., Barcelona (ES)

( * ) Notice: Subject to any disclaimer, the term of this patent is extended or adjusted under 35 U.S.C. 154(b) by 218 days.

(21) Appl. No.: 14/412,257

(22) PCT Filed: Jul. 4, 2013

(86) PCT No.: PCT/EP2013/064113
§ 371 (c)(1),
(2) Date: Dec. 31, 2014

(87) PCT Pub. No.: WO2014/006130
PCT Pub. Date: Jan. 9, 2014

(65) Prior Publication Data
US 2015/0166574 A1    Jun. 18, 2015

(30) Foreign Application Priority Data
Jul. 4, 2012 (EP) .................................. 12382269

(51) Int. Cl.
*C07D 513/04* (2006.01)
(52) U.S. Cl.
CPC ................................ *C07D 513/04* (2013.01)
(58) Field of Classification Search
CPC ................................................... C07D 513/04
See application file for complete search history.

(56) References Cited

U.S. PATENT DOCUMENTS 4,588,723 A    5/1986    Ingendoh

FOREIGN PATENT DOCUMENTS

| EP | 0141072 | 8/1984 |
|----|---------|--------|
| WO | WO 2007/098961 | 9/2007 |
| WO | WO 2009/040552 | 4/2009 |

OTHER PUBLICATIONS

CAS Registry Entry for Registry No. 1368484-89-2, which entered STN on Apr. 15, 2012.*
CAS Registry Entry for Registry No. 1177477-66-5, which entered STN on Aug. 28, 2009.*
Liu et al. Yale Journal of Biology and Medicine 2014, 87, 481-489.*
WebMD entry for Parkinson's Disease Prevention, obtained from http://www.webmd.com/parkinsons-disease/guide/parkinsons-disease-prevention on Jul. 19, 2012.*
Maurice et al. Pharmacology & Therapeutics 2009, 124, 195-206.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
CAS Registry Entry for Registry No. 1018585-05-1, which entered STN on Apr. 30, 2008.*
Bowen. et al., Pharmaceutica Acta Helvetiae, vol. 74, p. 211-218, 2000.
Dehaven-Hudkins, et al., European Journal of Pharmacology—Molecular Pharmacology Section, vol. 227, p. 371-378, 1992.
Haner, et al., Proc. Natl. Acad. Sci. USA. vol. 93, p. 8072-8077, Jul. 1996.
International Search Report for PCT/EP2013/064113 of Sep. 3, 2013.
Kaiser, Neurotransmissions, vol. 7, No. 1, p. 1-5, 1991.
Merskey, et al., Classification of Chronic Pain Second Edition, p. 210-213, 2002.
Quirionx, Tips, vol. 13, p. 85-86, Mar. 1992.
Ronsisvalle, et al., Pure Appl Chem, vol. 73, No. 9, p. 1499-1509, 2001.
Scribner, et al., Bioorganic and Medicinal Chemistry Letters vol. 18, p. 5253-5267, 2008.
Solomon, et al., Journal of Neuropsychiatry, vol. 1, No. 1, p. 7-15, Winter 1998.
Vu, et al., Journal Med. Chem. vol. 52, p. 1275-1283, 2009.
Walker, et al., Pharmacological Review, vol. 42, No. 4, p. 355-402, 2006.

* cited by examiner

*Primary Examiner* — Matthew Coughlin
(74) *Attorney, Agent, or Firm* — Hueschen and Sage

(57) ABSTRACT

The present invention relates to new imidazo[2,1-b]thiazole derivatives having a great affinity for sigma receptors, especially sigma-1 receptors, as well as to the process for the preparation thereof, to compositions comprising them, and to their use as medicaments.

24 Claims, No Drawings

IMIDAZO[2,1-B]THIAZOLE DERIVATIVES, THEIR PREPARATION AND USE AS MEDICAMENTS

FIELD OF THE INVENTION

The present invention relates to new imidazo[2,1-b]thiazole derivatives having a great affinity for sigma receptors, especially sigma-1 receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF-10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF-10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. The sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (e.g. nervous system, immune system, endocrine system, liver, kidney). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Different sigma receptor ligands have been reported.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009071657 also reports tricyclic triazolic compounds having good activity towards sigma receptors.

Some imidazo[2,1-b]thiazole derivatives with therapeutic activity have been disclosed so far in the prior art. For instance document WO 2009040552 imidazothiadiazoles for treating cancer via inhibition of protein kinases. CA 1053239 also discloses some imidazo[2,1-b]thiazole derivatives with antihyperglycaemic activity. WO2005079735 and US 20060156484 teaches among other compounds imidazo [2,1-b]thiazole derivatives although as dyeing agents for keratin. However, none of these references discloses the imidazo[2,1-b]thiazole derivatives of the present invention. In addition none of these references suggest that imidazo[2,1-b]thiazole derivatives can be active towards sigma receptors.

Nevertheless, there is still a need to find compounds having pharmacological activity towards the sigma receptor, being both effective and selective, and having good "drugability" properties, i.e. good pharmaceutical properties related to administration, distribution, metabolism and excretion.

SUMMARY OF THE INVENTION

The present invention discloses novel compounds with great affinity to sigma receptors which might be used for the treatment of sigma related disorders or diseases.

Specifically, it is an object of the present invention novel imidazo[2,1-b]thiazole derivatives of general formula (I):

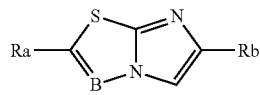

Another object of the invention is the different processes for preparation of compounds of general formula (I).

Another object of the invention refers to the use of such compounds of general formula (I) for the treatment or prophylaxis of sigma receptor mediated diseases or conditions, especially sigma-1 mediated diseases or conditions. Within the group of diseases or conditions mediated by the sigma receptor for which the compounds of the invention are effective diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are very good and are especially effective for the treatment and prophylaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to a compound of general formula (I):

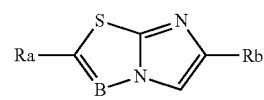

where
$R_a$ and $R_b$ independently represent a 5 or 6-membered aryl radical optionally substituted by a halogen or a branched or unbranched, saturated or unsaturated, optionally at least mono-substituted, alkyl radical $C_{1-6}$; a 5 or 6-membered heteroaryl radical having at least one heteroatom selected from N, O or S as ring member, optionally substituted by a halogen or a branched or unbranched, saturated or unsaturated, optionally at least mono-substituted, alkyl radical $C_{1-6}$; or the following moiety:

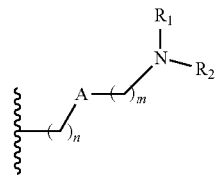

with the proviso that one of $R_a$ and $R_b$ represents this moiety and the other one represents 5 or 6-membered aryl radical optionally substituted by a halogen or a branched or unbranched, saturated or unsaturated, optionally at least mono-substituted, alkyl radical $C_{1-6}$; or a 5 or 6-membered heteroaryl radical having at least one heteroatom selected from N, O or S as ring member, optionally substituted by a halogen or a branched or unbranched, saturated or unsaturated, optionally at least mono-substituted, alkyl radical $C_{1-6}$ A is a C or O;
B is a C or N;
$R_1$ and $R_2$ independently represent a H; or $R_1$ and $R_2$ together with the bridging N form an 5 to 7-membered heterocyclic ring which can have at least one additional heteroatom selected from N, O or S and that can be optionally substituted by a branched or unbranched, saturated or unsaturated, aliphatic radical $C_{1-10}$ or by an aryl radical optionally substituted by an alkyl $C_{1-6}$, a halogen or an OH group;
n is 0, 1 or 2;
m is 0, 1, 2, 3 or 4;
with the proviso that when A is O m is different from 0; and
with the proviso that when B represents a C and $R_b$ represents a phenyl substituted by a halogen, $R_a$ cannot represent the moiety:

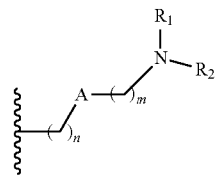

with $R_1$ and $R_2$ together with the bridging N forming a piperazine, or a pharmaceutically acceptable salt, isomer, prodrug or solvate thereof.

"Halogen" or "halo" as referred in the present invention represent fluorine, chlorine, bromine or iodine.

"Alkyl radicals", as referred to in the present invention, are saturated aliphatic radicals. They may be linear or branched and are optionally substituted. $C_{1-6}$ alkyl as expressed in the present invention means an alkyl radical of 1, 2, 3, 4, 5 or 6 carbon atoms.

An "aryl radical", as referred to in the present invention, is understood as meaning ring systems with at least one aromatic ring but without heteroatoms even in only one of the rings. These aryl radicals may optionally be mono- or polysubstituted by substitutents independently selected from a $C_{1-6}$ alkyl group, a linear or branched $C_{1-6}$ alkoxy group, an optionally at least mono-substituted phenyl group, —F, —Cl, —I, —Br, —CF$_3$, —CH$_2$F, —CHF$_2$, —CN, —OH, —SH, —NH$_2$, oxo, —(C=O)R', —SR', —SOR', —SO$_2$R', —N(C=O)OR', —NHR', —NR'R" whereby R' and optionally R" for each substituent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

A "heteroaryl radical", is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-6}$ alkyl group, a linear or branched $C_{1-6}$ alkoxy group, F, Cl, I, Br, CF$_3$, CH$_2$F, CHF$_2$, CN, OH, SH, NH$_2$, oxo, (C=O)R', SR', SOR', SO$_2$R', NHR', NR'R" whereby R' and optionally R" for each substituent independently represents a linear or branched $C_{1-6}$ alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, triazole, pyrazole, isoxazole, indole, benzotriazole, benzodioxolane, benzodioxane, benzimidazole, carbazole and quinazoline.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

"Cyclyl groups/radicals" or "cyclic systems", as defined in the present invention, comprise any saturated, unsaturated or aromatic carbocyclic ring systems which contain optionally at least one heteroatom as ring member and which are optionally at least mono-substituted. Cyclyl groups or cyclic systems preferably comprise aryl, heteroaryl, cyclyl, heterocyclyl and/or spiro ring systems.

"Heterocyclyl groups/radicals" or "heterocyclic ring or systems", as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$-alkoxy.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" or "pharmaceutically acceptable salt" is understood in particular, in the context of this invention, as salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals. Examples of physiologically tolerated salts of particular acids are salts of: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid picric acid and/or aspartic acid. Examples of physiologically tolerated salts of particular bases are salts of alkali metals and alkaline earth metals and with NH$_4$.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention the compounds of the invention have a general formula (Ia):

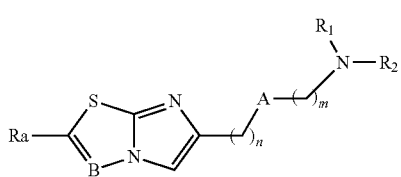
(Ia)

where $R_a$, $R_1$, $R_2$, A, B, n and m have the same meaning as for general formula (I).

In a yet more particular embodiment, compounds of the invention have a general formula I selected from (Iaa), (Iab), (Iac) or (Iad):

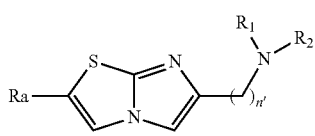
(Iaa)

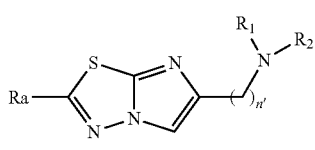
(Iab)

(Iac)

(Iad)

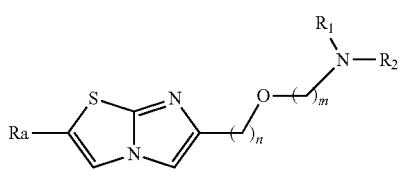

where $R_a$, $R_1$, $R_2$, n and m have the same meaning as for general formula (I) and n' are 1 or 2.

In another particular and preferred embodiment of the invention the compounds may have a general formula (Ib):

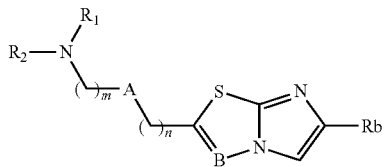
(Ib)

where $R_b$, $R_1$, $R_2$, A, B, n and m have the same meaning as for general formula (I).

A still more particular embodiment is represented by compounds of general formula (Iba), (Ibb), (Ibc) or (Ibd):

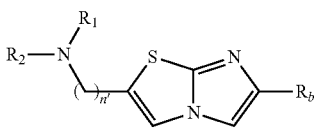
(Iba)

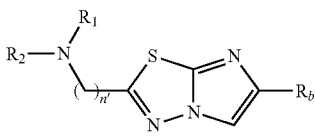
(Ibb)

(Ibc)

(Ibd)

where $R_b$, $R_1$, $R_2$, n and m have the same meaning as for general formula (I) and n' is 1 or 2.

In another preferred embodiment of the invention, $R_a$ or $R_b$ in either compounds of formula (I), (Ia) or (Ib) may represents a group selected from:

where $R_c$ represents H, a $C_{1-6}$ alkyl, a halogen or an —OR'group where R' represents a linear or branched $C_{1-6}$-alkyl group.

In yet another preferred embodiment of the invention $R_1$ and $R_2$ together with the bridging N form a group selected from:

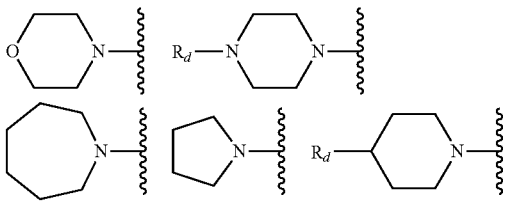

where $R_d$ represents a H, a $C_{1-6}$ alkyl or a phenyl group optionally substituted by a $C_{1-6}$ alkyl, a halogen or an —OH group.

In a particular and preferred embodiment A is C and m and n are both 0 for compounds of formula (I), (Ia) or (Ib).

In another particular and preferred embodiment of compounds of formula (I), (Ia) or (Ib) A is O, n is 1 and m is 2.

In preferred variants of the invention, the sigma ligand of formula (I) is selected from:
   [1] 4-((2-phenylimidazo[2,1-b]thiazol-6-yl)methyl)morpholine maleate,

[2] 6-((4-methylpiperazin-1-yl)methyl)-2-(pyridin-4-yl) imidazo[2,1-b]thiazole maleate,
[3] 6-(2-(4-methylpiperazin-1-yl)ethyl)-2-phenylimidazo [2,1-b]thiazole maleate,
[4] 6-((2-(azepan-1-yl)ethoxy)methyl)-2-phenylimidazo [2,1-b][1,3,4]thiadiazole maleate,
[5] 2-((4-methylpiperazin-1-yl)methyl)-6-phenylimidazo [2,1-b]thiazole maleate,
[6] 6-(azepan-1-ylmethyl)-2-phenylimidazo[2,1-b]thiazole maleate,
[7] 6-((4-methylpiperazin-1-yl)methyl)-2-phenylimidazo [2,1-b]thiazole maleate,
[8] 4-(2-((2-phenylimidazo[2,1-b]thiazol-6-yl)methoxy) ethyl)morpholine maleate,
[9] 6-((2-(azepan-1-yl)ethoxy)methyl)-2-phenylimidazo [2,1-b]thiazole maleate,
[10] 2-phenyl-6-((2-(pyrrolidin-1-yl)ethoxy)methyl)imidazo[2,1-b]thiazole maleate,
[11] 6-((4-methylpiperazin-1-yl)methyl)-2-phenylimidazo [2,1-b][1,3,4]thiadiazole maleate,
[12] 2-(azepan-1-ylmethyl)-6-phenylimidazo[2,1-b]thiazole maleate,
[13] 2-(4-fluorophenyl)-6-((4-methylpiperazin-1-yl) methyl)imidazo[2,1-b]thiazole maleate,
[14] 3-(1-((2-phenylimidazo[2,1-b]thiazol-6-yl)methylpiperidin-4-yl)phenol maleate Any compound referred to herein is intended to represent such specific compound as well as certain variations or forms. In particular, compounds referred to herein may have asymmetric centers and therefore exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

In another aspect, the invention refers to the processes for obtaining the compounds of general formula (I). Four different procedures have been developed for obtaining all the compound derivatives of the invention, herein the procedures will be explained below in methods A to D.

Method A

Method A represents the process for preparing compounds of general formula (Iaa) and formula (Iab), that is, compounds of formula (Ia) where B can be C or N but A represents a C and n is always 1 or 2.

The process for the preparation of a compound of general formula (Iaa) or (Iab) according to method A:

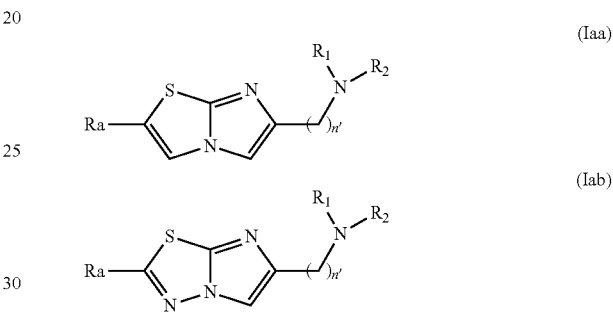

where $R_a$, $R_1$ and $R_2$ have the same meanings as for formula (I) and n' is 1 or 2, the process comprises:

a) the reaction between a compound of general formula (II):

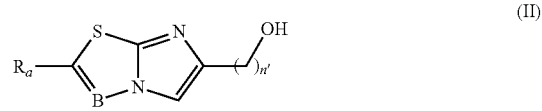

where B is a C or a N, with a sulphonide halide such as methanesulphonide chloride, and b) the reaction between the resulting compound with a compound of general formula (III):

$R_1R_2NH$                                        (III)

the reactions being carried out in the presence of a base such as triethylamine in a suitable organic solvent such as dichloromethane.

The general route for the synthesis of compounds of formula (Iaa) and (Iab) by method A is represented in scheme 1:

Scheme 1

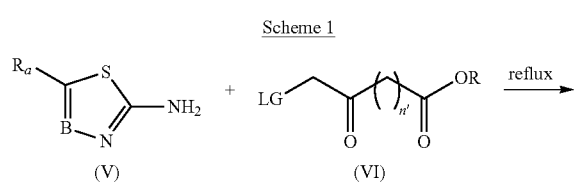

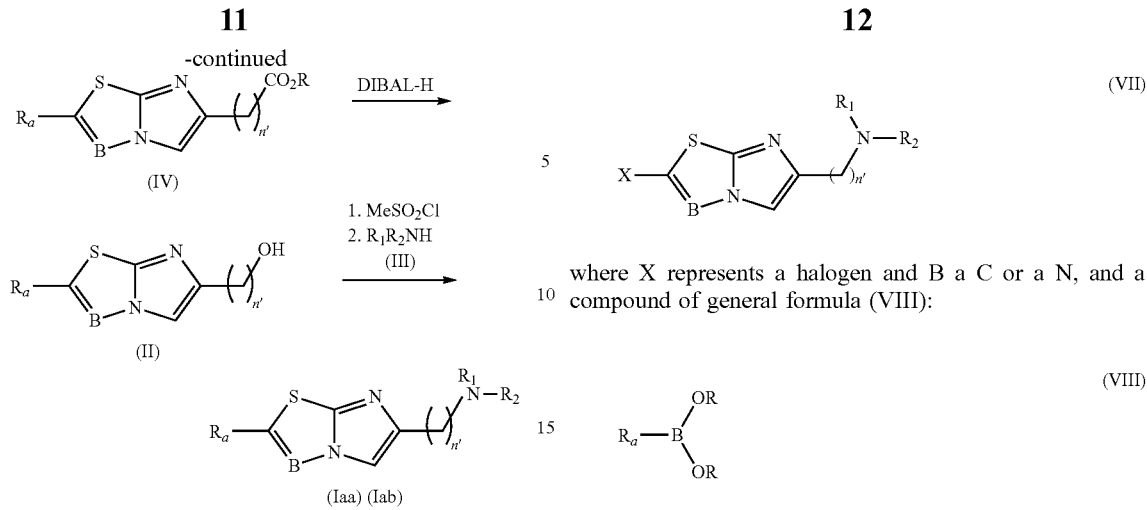

Compounds of formula (Iaa) and (Iab) as expressed in scheme 1 are prepared by a nucleophilic substitution between a compound of formula (II), converted to the corresponding mesylate by treatment with methanesulfonyl chloride, and a convenient substituted amine (III). This reaction is conducted in the presence of a base such as triethylamine and in a suitable solvent such as $CH_2Cl_2$ at room temperature.

In turn, compounds of formula (II) are obtained by reduction of compounds of formula (IV) by methods generally known by the skilled in the art (*Bioorg. Med. Chem. Lett.* 2008, 18, 5263).

Amines (III) are commercially available.

Compounds of formula (IV) are obtained by condensation between compounds of formula (V) and compounds of formula (VI) by methods generally known by the skilled in the art (*J. Med. Chem.* 2009, 52, 1275; WO2007019344).

Compounds (V) are commercially available or obtained by reaction between a convenient substituted acetaldehyde and thiourea as described in WO2008144767.

Oxoacid derivatives (VI) are commercially available.

Method B

Method B represents a different process for preparing compounds of general formula (Iaa) and formula (Iab), that is, compounds of formula (Ia) where B can be C or N but A represents a C and n is always 1 or 2.

Method B represents a process for the preparation of a compound of general formula (Iaa) or (Iab):

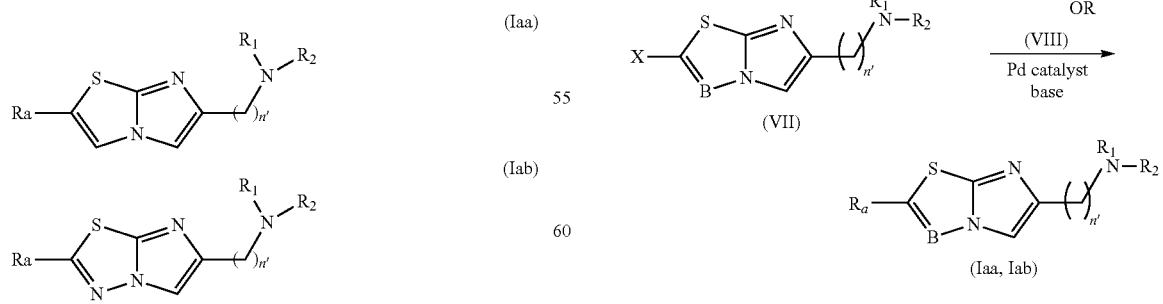

where $R_a$, $R_1$ and $R_2$ have the same meanings as for formula (I) and n' is 1 or 2, the process comprising the reaction between a compound of general formula (VII):

(VII)

where X represents a halogen and B a C or a N, and a compound of general formula (VIII):

(VIII)

where each R represent independently represent a hydrogen, a $C_{1-6}$ alkyl or both R together with the bridging boron form a boronic cyclic ester such as a boronic acid pinacol ester in the presence of a suitable catalyst, such as a palladium catalyst, and a base such as potassium carbonate, phosphate hydroxide or alkoxides in an organic reaction-inert solvent such as THF, DMSO, DMF, diethyl ether or ethanol.

The general route for the synthesis of compounds of formula (Iaa) and (Iab) by method B is represented in scheme 2:

Scheme 2

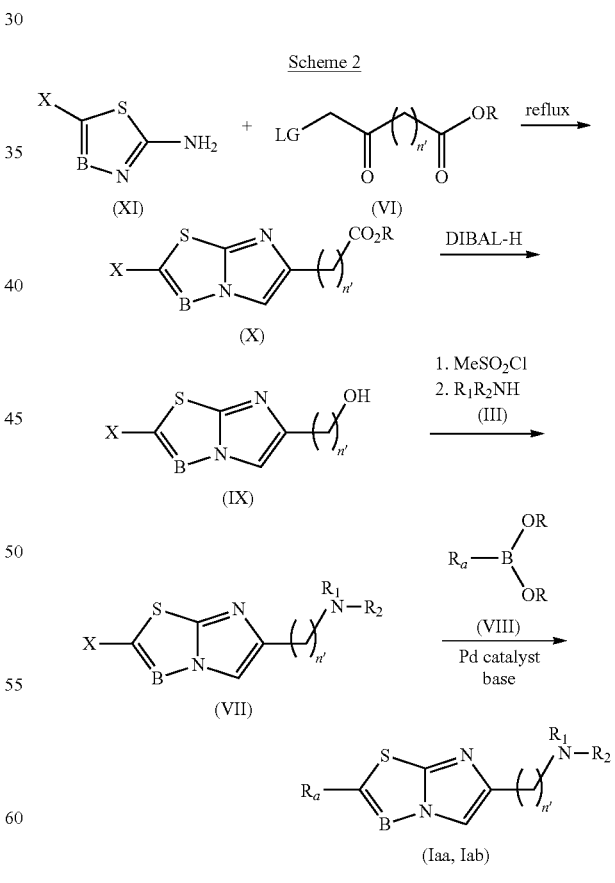

Compounds of formula (Iaa) and (Iab) are obtained by a Suzuki coupling of a compound of formula (VII) with organoboronic acid derivatives (VIII) in the presence of a palladium catalyst, a base and a suitable solvent. This reaction is conducted in a reaction-inert solvent, such as tetrahydrofuran (THF), dimethylsulfoxide (DMSO), dimethylformamide (DMF), diethyl ether, ethanol, etc. The palladium catalyst may be selected from a Pd(II) or Pd(0) catalyst, e.g. $Pd(OAc)_2$, $Pd(PPh_3)_4$ or Pd/C. The base that is involved in the coordination sphere of the palladium and in the acceleration of the transmetallation step may be selected from a negatively charged base, such as sodium or potassium carbonate, phosphate, hydroxide, alkoxides, etc.

In turn, compounds of formula (VII) are obtained by nucleophilic substitution between a compound of formula (IX), converted to the corresponding mesylate by treatment with methanesulfonyl chloride, and a convenient substituted amine (III). This reaction is conducted in the presence of a base such as triethylamine and in a suitable solvent such as $CH_2Cl_2$ at room temperature.

Organoboronic acid derivatives (VIII) are commercially available

Compounds of formula (IX) are obtained by reduction of compounds of formula (X) by methods generally known by the skilled in the art (*Bioorg. Med. Chem. Lett.* 2008, 18, 5263).

Amines (III) are commercially available.

Compounds of formula (X) are obtained by condensation between compounds of formula (XI) and compounds of formula (VI) by methods generally known by the skilled in the art (*J. Med. Chem.* 2009, 52, 1275; WO2007019344).

Compounds (XI) and oxoacid derivatives (VI) are commercially available.

Method C

Method C represents the process for preparing compounds of general formula (Iac) and formula (Iad), that is, compounds of formula (Ia) where B can be C or N but A represents an O.

The process for the preparation of a compound of general formula (Iac) or (Iad) by method C:

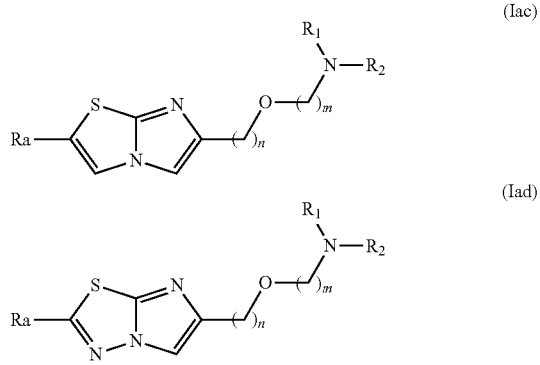

(Iac)

(Iad)

where $R_a$, $R_1$, $R_2$ n and m have the same meanings as for formula (I), comprises the reaction between a compound of general formula (II):

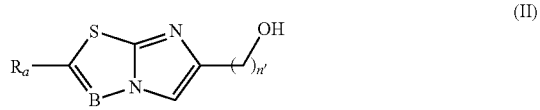

(II)

where B is C or a N, and a compound of general formula (XII):

(XII)

where LG is a suitable leaving group, preferably a halogen, in the presence of a base in an organic solvent.

The general route for the synthesis of compounds of formula (Iac) and (Iad) by method C is represented in scheme 3:

Scheme 3

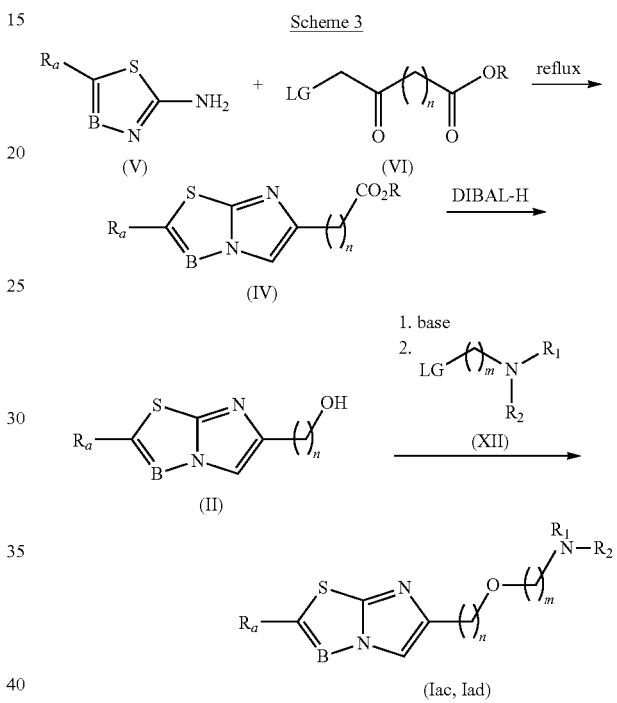

(Iac, Iad)

Compounds of general formula (Iac) and formula (Iad) are obtained by reaction of a compound of formula (II) with a compound of formula (XII) in the presence of a base and a suitable solvent; where LG represents a leaving group that may be selected from a halide, e.g. bromide or chloride, or an arylsulfonyl group, e.g. mesylate, triflate, or tosylate, and the like. This reaction is conducted under phase transfer conditions. The base is strong enough to detract a hydrogen from the hydroxyl group, for example a negatively charged base, such as sodium or potassium carbonate, phosphate, hydroxide, alkoxides, etc.

Compounds of formula (II) are obtained by reduction of compounds of formula (IV) by methods generally known by the skilled in the art (*Bioorg. Med. Chem. Lett.* 2008, 18, 5263).

Compounds of formula (XII) are commercially available.

Compounds of formula (IV) are obtained by condensation between compounds of formula (V) and compounds of formula (VI) by methods generally known by the skilled in the art (*J. Med. Chem.* 2009, 52, 1275; WO2007019344).

Compounds (V) are commercially available or obtained by reaction between a convenient substituted acetaldehyde and thiourea as described in WO2008144767.

Oxoacid derivatives (VI) are commercially available.

Method D

Method D represents the process for preparing compounds of general formula (Iba) and formula (Ibb), that is, compounds of formula (Ib) where B can be C or N but A represents a C and n is always 1 or 2.

Method B is represents a process for the preparation of a compound of general formula (Iba) or (Ibb):

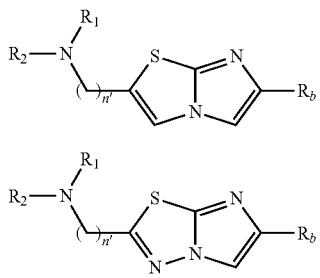

where $R_b$, $R_1$ and $R_2$ have the same meanings as for formula (I) and n' is 1 or 2, the process comprising:

a) the reaction between a compound of general formula (XIII):

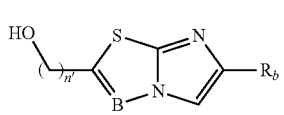

where B is C or N, with a sulphonide halide such as methansulphonidde chloride, b) the reaction of the resulting compound with a compound of general formula (III):

 (III)

the reactions being carried out in the presence of a base such as triethylamine in an organic solvent such as dichloromethane.

The general route for the synthesis of compounds of formula (Iba) and (Ibb) by method D is represented in scheme 4:

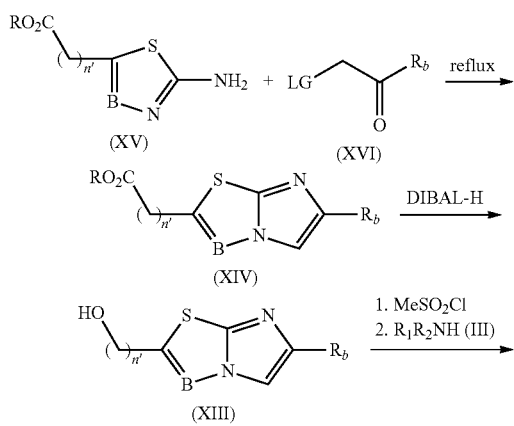

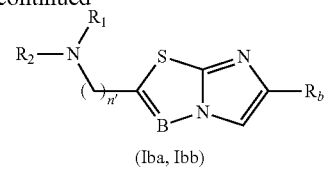

Compounds of formula (Iba) and (Ibb) are prepared by nucleophilic substitution between a compound of formula (XIII), converted to the corresponding mesylate by treatment with methanesulfonyl chloride, and a convenient substituted amine (III). This reaction is conducted in the presence of a base such as triethylamine and in a suitable solvent such as $CH_2Cl_2$ at room temperature.

In turn, compounds of formula (XIII) are obtained by reduction of compounds of formula (XIV) by methods generally known by the skilled in the art (Bioorg. Med. Chem. Lett. 2008, 18, 5263).

Amines (III) are commercially available.

Compounds of formula (XIV) are obtained by condensation between compounds of formula (XV) and compounds of formula (XVI) by methods generally known by the skilled in the art (Bioorg. Med. Chem. Lett. 2008, 18, 5263; J. Med. Chem. 2009, 52, 1275; WO2007019344).

Compounds (XV) and arylketones (XVI) are commercially available.

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. Therefore, compounds of general formula (I) are useful as medicaments.

They are suitable for the treatment and the prophylaxis of disorders and diseases mediated by sigma receptors, especially, sigma-1 receptors. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases.

The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and prophylaxis of allodynia and more specifically mechanical or thermal allodynia.

In another preferred embodiment compounds of the invention are used for the treatment and prophylaxis of hyperalgesia.

In yet another preferred embodiment compounds of the invention are used for the treatment and prophylaxis of neuropathic pain and more specifically for the treatment and prophylaxis of hyperpathia.

A related aspect of the invention refers to the use of compounds of formula (I) for the manufacture of a medicament for the treatment of disorders and diseases mediated by sigma receptors, as explained before.

Another aspect of the invention is a pharmaceutical composition which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the sigma receptor and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, drageés, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The respective medicament may—depending on its route of administration—also contain one or more auxiliary substances known to those skilled in the art. The medicament according to the present invention may be produced according to standard procedures known to those skilled in the art.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

Example 1 (Method A):

Synthesis of 4-((2-phenylimidazo[2,1-b]thiazol-6-yl)methyl)morpholine maleate a) Synthesis of ethyl 2-phenylimidazo[2,1-b]thiazole-6-carboxylate

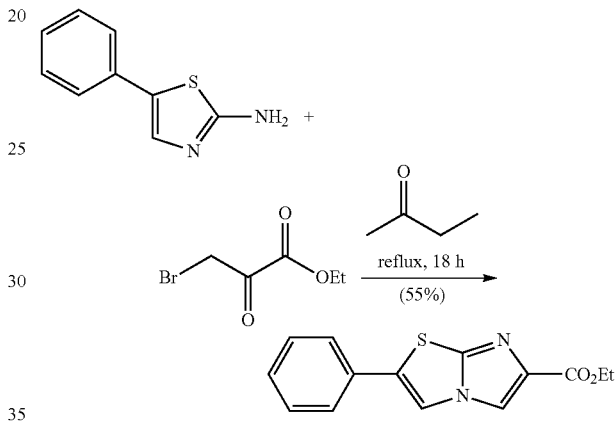

A solution of 5-phenylthiazol-2-amine (5.0 g, 28.37 mmol) and ethyl bromopiruvate (5.3 mL, 42.56 mmol) in methyl ethyl ketone (250 mL) was refluxed overnight under argon atmosphere. The reaction mixture was evaporated to dryness. The crude product was purified by silica gel column chromatography ($CH_2Cl_2$:MeOH mixtures of increasing polarity as eluent) to afford the desired product (4.24 g, 55%).

$^1$H-NMR (DMSO-$d_6$, 300 MHz) δ: 8.45 (s, 1H), 8.39 (s, 1H), 7.66 (m, 2H), 7.52-7.42 (m, 3H), 4.26 (d, J=7.2 Hz, 2H), 1.29 (t, J=7.2 Hz, 3H) ppm.

EI-MS m/z: 272.1 (M).

b) Synthesis of (2-phenylimidazo[2,1-b]thiazol-6-yl)methanol

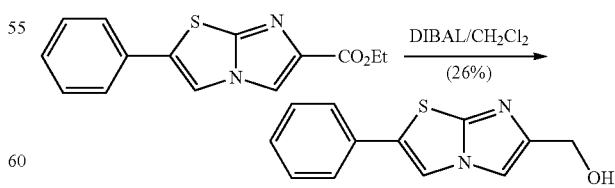

A solution of DIBAL (1.0 M in $CH_2Cl_2$, 46.7 mL, 46.7 mmol) was added to a solution of ethyl 2-phenylimidazo[2,1-b]thiazole-6-carboxylate (4.2 g, 15.57 mmol) in $CH_2Cl_2$ (130 mL) cooled to 0° C. under argon atmosphere. The resulting mixture was stirred for 2 h. The reaction mixture was diluted with water and filtered through Celite®. The layers were separated and the organic phase, was dried over $Na_2SO_4$, and evaporated to dryness. The crude product was purified by silica gel column chromatography ($CH_2Cl_2$:MeOH mixtures of increasing polarity as eluent) to afford the desired product (929 mg, 26%).

$^1$H-NMR (DMSO-$d_6$, 400 MHz) δ: 8.39 (s, 1H), 7.60 (m, 3H), 7.46 (t, J=8 Hz, 2H), 7.37 (t, J=8 Hz, 1H), 5.07 (t, J=5.8 Hz, 1H), 4.45 (d, J=4.8 Hz, 2H) ppm.

EI-MS m/z: 230.1 (M).

c) Synthesis of 4-((2-phenylimidazo[2,1-b]thiazol-6-yl)methyl)morpholine maleate

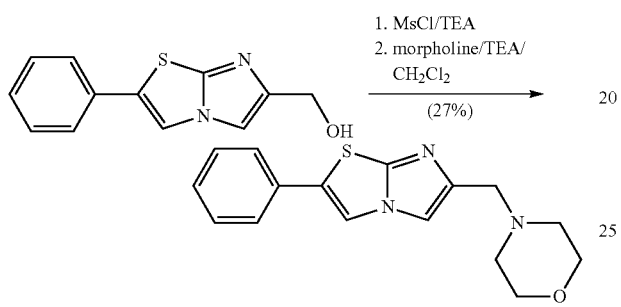

Methanesulfonyl chloride (0.1 mL, 0.99 mmol) and triethylamine (0.14 mL, 0.99 mmol) were added to a solution of (2-phenylimidazo[2,1-b]thiazol-6-yl)methanol (228 mg, 0.99 mmol) in $CH_2Cl_2$ (15 mL) cooled to 0° C. under argon atmosphere. The resulting mixture was stirred for 15 minutes. The reaction mixture was diluted with brine and extracted with $CH_2Cl_2$. The organic extract was dried with $Na_2SO_4$ and evaporated to dryness. To a solution of the previous residue in $CH_2Cl_2$ (8 mL), morpholine (0.082 mL, 0.94 mmol) and triethylamine (0.13 mL, 0.94 mmol) was added. The resulting mixture was stirred overnight. The reaction mixture was diluted with water and extracted with $CH_2Cl_2$. The organic extract was dried with $Na_2SO_4$ and evaporated to dryness. The crude product was purified by silica gel column chromatography ($CH_2Cl_2$:MeOH mixtures of increasing polarity as eluent) to afford the desired product (80 mg, 27%). The product was converted into the corresponding maleate salt by adding maleic acid (26 mg, 0.22 mmol) in acetone (0.35 mL), followed by filtration of the resulting solid and drying under vacuum.

$^1$H-NMR (CDCl$_3$, 400 MHz) δ: 8.49 (s, 1H), 7.90 (m, 1H), 7.63 (m, 2H), 7.49 (t, J=7.4 Hz, 2H), 7.41 (t, J=7.4 Hz, 1H), 6.04 (s, 2H), 3.65 (m, 2H), 3.31 (m, 8H) ppm.

ESI(+)-HRMS: 300.1164 [M+H]$^+$.

Example 2 (Method B):

Synthesis of 6-((4-methylpiperazin-1-yl)methyl)-2-(pyridin-4-yl)imidazo[2,1-b]thiazole maleate a) Synthesis of ethyl 2-bromoimidazo[2,1-b]thiazole-6-carboxylate

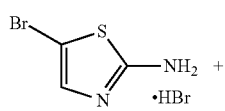

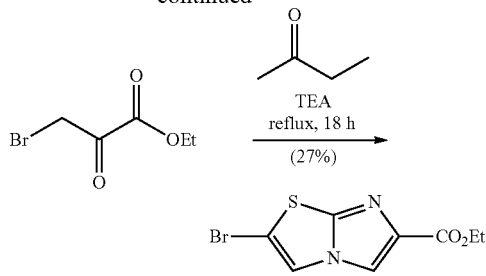

A mixture of 5-bromothiazol-2-amine hydrobromide (5.0 g, 19.23 mmol), ethyl bromopiruvate (3.6 mL, 28.85 mmol) and triethylamine (4.0 mL, 28.85 mmol) in methyl ethyl ketone (200 mL) was refluxed overnight under argon atmosphere. The reaction mixture was evaporated to dryness. The crude product was purified by silica gel column chromatography (hexane:EtOAc mixtures of increasing polarity as eluent) to afford the desired product (1.46 g, 27%).

$^1$H-NMR (DMSO-$d_6$, 300 MHz) δ: 8.34 (s, 1H), 8.25 (s, 1H), 4.25 (q, J=6.9 Hz, 2H), 1.27 (t, J=7.2 Hz, 3H) ppm.

EI-MS m/z: 273.9 (M).

b) Synthesis of (2-bromoimidazo[2,1-b]thiazol-6-yl)methanol

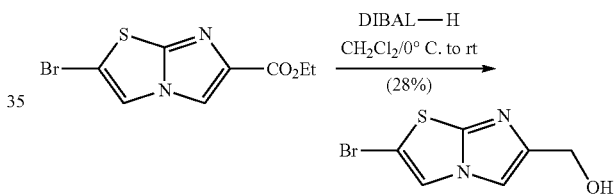

A solution of DIBAL (1.0 M in $CH_2Cl_2$, 15.8 mL, 15.81 mmol) was added to a solution of ethyl 2-bromoimidazo[2,1-b]thiazole-6-carboxilate (1.45 g, 5.27 mmol) in $CH_2Cl_2$ (100 mL) under argon atmosphere. The resulting mixture was stirred for 4 h. The reaction mixture was diluted with water and filtered through Celite®. The layers were separated and the organic phase, was dried over $Na_2SO_4$ and evaporated to dryness. The crude product was purified by silica gel column chromatography ($CH_2Cl_2$:MeOH mixtures of increasing polarity as eluent) to afford the desired product (341 mg, 28%).

$^1$H-NMR (DMSO-$d_6$, 400 MHz) δ: 8.18 (s, 1H), 7.58 (s, 1H), 5.06 (t, J=6.4 Hz, 1H), 4.41 (d, J=4.4 Hz, 2H) ppm.

EI-MS m/z: 231.9 (M).

c) Synthesis of 2-bromo-6-((4-methylpiperazin-1-yl)methyl)imidazo[2,1-b]thiazole

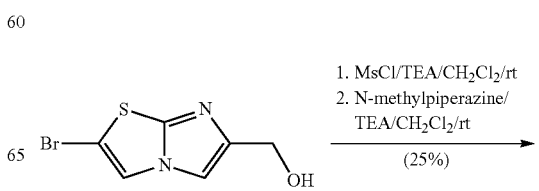

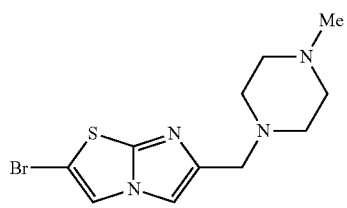

Methanesulfonyl chloride (0.16 mL, 1.44 mmol) and triethylamine (0.2 mL, 1.44 mmol) was added to a solution of (2-bromoimidazo[2,1-b]thiazol-6-yl)methanol (335 mg, 1.44 mmol) in $CH_2Cl_2$ (8 mL) under argon atmosphere. The resulting mixture was stirred for 15 minutes. The reaction mixture was diluted with brine and extracted with $CH_2Cl_2$. The organic extract was dried with $Na_2SO_4$ and evaporated to dryness. To a solution of the previous residue in $CH_2Cl_2$ (8 mL), N-methylpiperazine (0.16 mL, 1.44 mmol) and triethylamine (0.2 mL, 1.44 mmol) was added. The resulting mixture was stirred for 20 h. The reaction mixture was diluted with water and extracted with $CH_2Cl_2$. The organic extract was dried with $Na_2SO_4$ and evaporated to dryness. The crude product was purified by silica gel column chromatography ($EtOAc/NH_3$:MeOH mixtures of increasing polarity as eluent) to afford the desired product (114 mg, 25%).

$^1$H-NMR ($CDCl_3$, 400 MHz) δ: 7.43 (s, 1H), 7.32 (s, 1H), 3.58 (s, 2H), 2.58 (m, 4H), 2.48 (m, 4H), 2.28 (s, 3H) ppm.
EI-MS m/z: 314.0 (M).

d) Synthesis of 6-((4-methylpiperazin-1-yl)methyl)-2-(pyridin-4-yl)imidazo[2,1-b]thiazole maleate

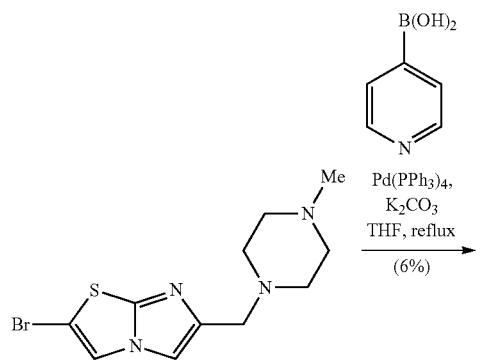

A mixture of 2-bromo-6-((4-methylpiperazin-1-yl)methyl)imidazo[2,1-b]thiazole (86 mg, 0.27 mmol), $Pd(PPh_3)_4$ (79 g, 0.07 mmol), 4-pyridineboronic acid (43 mg, 0.3 mmol) and 2 M solution of $K_2CO_3$ (0.7 mL) in THF (7 mL) was refluxed with stirring for 1 day under argon atmosphere. The reaction mixture was poured into water and extracted with 1N HCl. The aqueous layers were basified with 2N NaOH and extracted with EtOAc. The organic layers were dried with $Na_2SO_4$ and evaporated to dryness. Purification of the residue by silica gel column chromatography ($EtOAc/NH_3$:MeOH mixtures of increasing polarity as eluent) afforded the desired product (5 mg, 6%). The product was converted into the corresponding maleate salt by adding maleic acid (1.0 equiv) in acetone, followed by filtration of the resulting solid and drying under vacuum.

$^1$H-NMR (DMSO-$d_6$, 400 MHz) δ: 8.75 (s, 1H), 8.64 (d, J=6.4 Hz, 2H), 7.77 (m, 1H), 7.61 (d, J=6 Hz, 2H), 6.03 (s, 2H), 3.65 (m, 2H), 3.30 (m, 4H), 3.03 (m, 4H), 2.71 (m, 3H) ppm.
ESI(+)-HRMS: 314.1434 [M+H]$^+$.

Example 3 (Method A):

Synthesis of 6-(2-(4-methylpiperazin-1-yl)ethyl)-2-phenylimidazo[2,1-b]thiazole maleate a) Synthesis of ethyl 2-(2-phenylimidazo[2,1-b]thiazol-6-yl)acetate

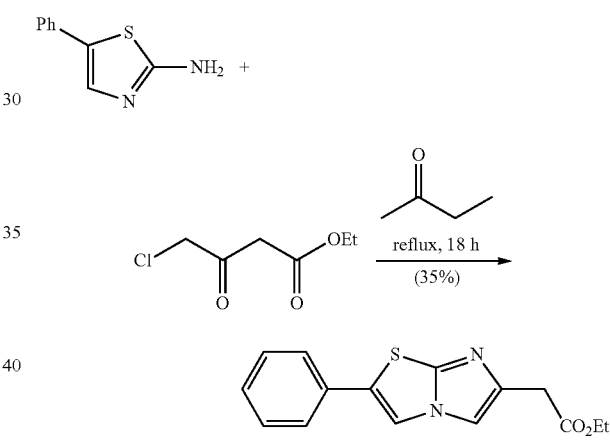

A mixture of 5-phenylthiazol-2-amine (500 mg, 2.84 mmol) and ethyl 4-chloro-3-oxobutanoate (0.58 mL, 4.26 mmol) in methyl ethyl ketone (50 mL) was refluxed overnight under argon atmosphere. The reaction mixture was evaporated to dryness. The crude product was purified by silica gel column chromatography ($CH_2Cl_2$:MeOH mixtures of increasing polarity as eluent) to afford the desired product (272 mg, 35%).

$^1$H-NMR (DMSO, 400 MHz) δ: 8.40 (s, 1H), 7.65 (s, 1H), 7.60 (m, 2H), 7.47 (m, 2H), 7.38 (m, 1H), 4.08 (q, J=7.2 Hz, 2H), 3.67 (s, 2H), 1.19 (t, J=7 Hz, 3H) ppm.
EI-MS m/z: 286.1 (M).

b) Synthesis of 2-(2-phenylimidazo[2,1-b]thiazol-6-yl)ethanol

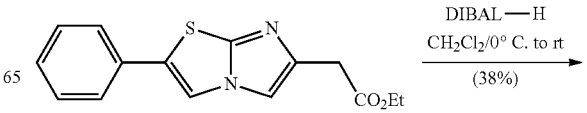

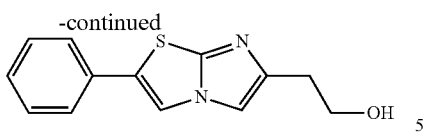

A solution of DIBAL (1.0 M in CH$_2$Cl$_2$, 5.1 mL, 5.1 mmol) was added to a solution of ethyl 2-(2-phenylimidazo[2,1-b]thiazol-6-yl)acetate (486 mg, 1.7 mmol) in CH$_2$Cl$_2$ (10 mL) under argon atmosphere. The resulting mixture was stirred for 5 h. The reaction mixture was diluted with water and filtered through Celite®. The layers were separated and the organic phase was dried over Na$_2$SO$_4$ and evaporated to dryness. The crude product was purified by silica gel column chromatography (CH$_2$Cl$_2$:MeOH mixtures of increasing polarity as eluent) to afford the desired product (156 mg, 38%).

$^1$H-NMR (DMSO, 400 MHz) δ: 8.37 (s, 1H), 7.60 (m, 2H), 7.52 (s, 1H), 7.46 (m, 2H), 7.36 (m, 1H), 4.60 (t, J=5.6 Hz, 1H), 3.66 (m, 2H), 2.72 (t, J=6.8 Hz, 2H) ppm.

EI-MS m/z: 244.1 (M).

c) Synthesis of 6-(2-(4-methylpiperazin-1-yl)ethyl)-2-phenylimidazo[2,1-b]thiazole maleate

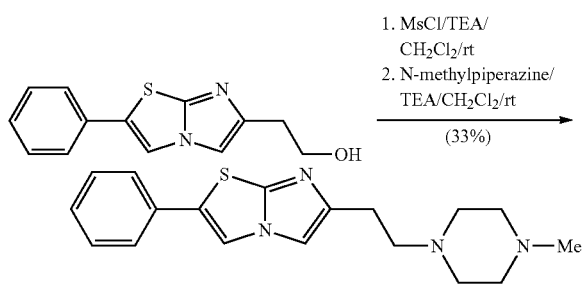

Methanesulfonyl chloride (0.048 mL, 0.62 mmol) and triethylamine (0.087 mL, 0.62 mmol) was added to a solution of 2-(2-phenylimidazo[2,1-b]thiazol-6-yl)ethanol (152 mg, 0.62 mmol) in CH$_2$Cl$_2$ (3 mL) cooled to 0° C. under argon atmosphere. The resulting mixture was stirred for 15 minutes. The reaction mixture was diluted with brine and extracted with CH$_2$Cl$_2$. The organic extract was dried with Na$_2$SO$_4$ and evaporated to dryness. To a solution of the previous residue in CH$_2$Cl$_2$ (3 mL), N-methylpiperazine (0.07 mL, 0.62 mmol) and triethylamine (0.087 mL, 0.62 mmol) was added. The resulting mixture was stirred overnight. The reaction mixture was diluted with water and extracted with CH$_2$Cl$_2$. The organic extract was dried with Na$_2$SO$_4$ and evaporated to dryness. The crude product was purified by silica gel column chromatography (CH$_2$Cl$_2$:MeOH mixtures of increasing polarity as eluent) to afford the desired product (68 mg, 33%). The product was converted into the corresponding maleate salt by adding maleic acid (24 mg, 0.21 mmol) in acetone (0.4 mL), followed by filtration of the resulting solid and drying under vacuum.

$^1$H-NMR (DMSO-d$_6$, 400 MHz) δ: 8.39 (s, 1H), 7.56 (m, 3H), 7.46 (m, 2H), 7.38 (m, 1H), 6.12 (s, 2H), 3.30 (m, 8H), 2.82 (m, 4H), 2.66 (m, 4H) ppm.

ESI(+)-HRMS: 327.1644 [M+H]+.

Example 4 (Method C):

Synthesis of 6-((2-(azepan-1-yl)ethoxy)methyl)-2-phenylimidazo[2,1-b][1,3,4]thiadiazole maleate a) Synthesis of ethyl 2-phenylimidazo[2,1-b][1,3,4]thiadiazole-6-carboxylate

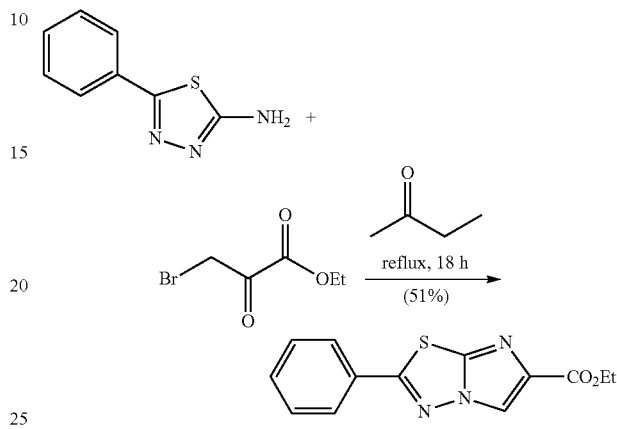

A mixture of 5-phenyl-1,3,4-thiadiazol-2-amine (489 mg, 2.76 mmol) and ethyl bromopiruvate (0.58 mL, 4.14 mmol) in methyl ethyl ketone (25 mL) was refluxed overnight under argon atmosphere. The reaction mixture was evaporated to dryness. The crude product was purified by silica gel column chromatography (CH$_2$Cl$_2$:MeOH mixtures of increasing polarity as eluent) to afford the desired product (386 g, 51%).

$^1$H-NMR (DMSO-d$_6$, 400 MHz) δ: 8.86 (s, 1H), 7.95 (m, 2H), 7.64-7.59 (m, 3H), 4.28 (q, J=7.2 Hz, 2H), 1.29 (t, J=7 Hz, 3H) ppm.

EI-MS m/z: 273.1 (M).

b) Synthesis of (2-phenylimidazo[2,1-b][1,3,4]thiadiazol-6-yl)methanol

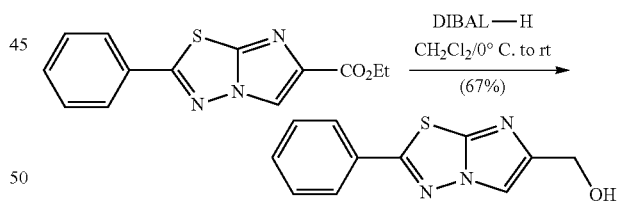

A solution of DIBAL (1.0 M in CH$_2$Cl$_2$, 7.6 mL, 7.58 mmol) was added to a solution of ethyl 2-phenylimidazo[2,1-b][1,3,4]thiadiazole-6-carboxylate (691 g, 2.53 mmol) in CH$_2$Cl$_2$ (50 mL) under argon atmosphere. The resulting mixture was stirred for 3 h. The reaction mixture was diluted with water and filtered through Celite®. The layers were separated and the organic phase was dried over Na$_2$SO$_4$ and evaporated to dryness. The crude product was purified by silica gel column chromatography (CH$_2$Cl$_2$:MeOH mixtures of increasing polarity as eluent) to afford the desired product (393 mg, 67%).

$^1$H-NMR (DMSO-d$_6$, 400 MHz) δ: 8.01 (s, 1H), 7.90 (m, 2H), 7.59-7.56 (m, 3H), 5.17 (t, J=5.6 Hz, 1H), 4.47 (d, J=5.6 Hz, 2H) ppm.

EI-MS m/z: 231.0 (M).

c) Synthesis of 6-((2-(azepan-1-yl)ethoxy)methyl)-2-phenylimidazo[2,1-b][1,3,4]thiadiazole maleate

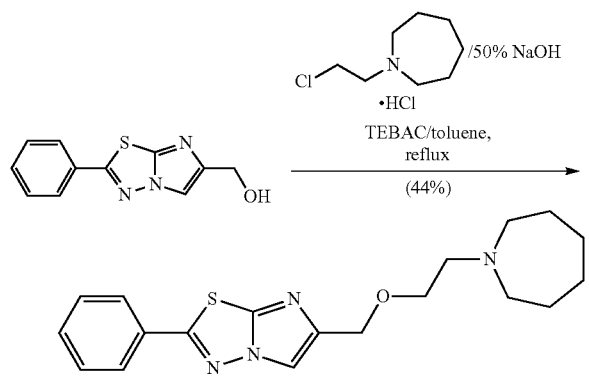

1-(2-Chloroethyl)azepane hydrochloride (514 mg, 2.59 mmol), 50% NaOH (10.4 mL, 12.97 mmol), and a catalytic amount of benzyltriethylammonium chloride were added to a solution of (2-phenylimidazo[2,1-b][1,3,4]thiadiazol-6-yl)methanol (120 mg, 0.52 mmol) in toluene (3 mL) under argon atmosphere. The resulting mixture was refluxed for 6 h. The reaction mixture was diluted with water and extracted with EtOAc. The organic extracts were dried with $Na_2SO_4$ and evaporated to dryness. The crude product was purified by silica gel column chromatography (EtOAc:MeOH mixtures of increasing polarity as eluent) to afford the desired product (393 mg, 67%). The product was converted into the corresponding maleate salt by adding maleic acid (27 mg, 0.23 mmol) in acetone (0.25 mL), followed by filtration of the resulting solid and drying under vacuum.

$^1$H-NMR (DMSO-$d_6$, 300 MHz) δ: 9.24 (s, 1H), 8.27 (s, 1H), 7.94 (m, 2H), 7.62 (m, 3H), 6.00 (s, 2H), 4.55 (s, 2H), 3.78 (t, J=5.1 Hz, 2H), 3.31 (m, 6H), 1.76 (m, 4H), 1.59 (m, 4H) ppm.

ESI(+)-HRMS: 357.1746 [M+H]$^+$.

Example 5 (Method D):

Synthesis of 2-((4-methylpiperazin-1-yl)methyl)-6-phenylimidazo[2,1-b]thiazole maleate a) Synthesis of (6-phenylimidazo[2,1-b]thiazol-2-yl)methanol

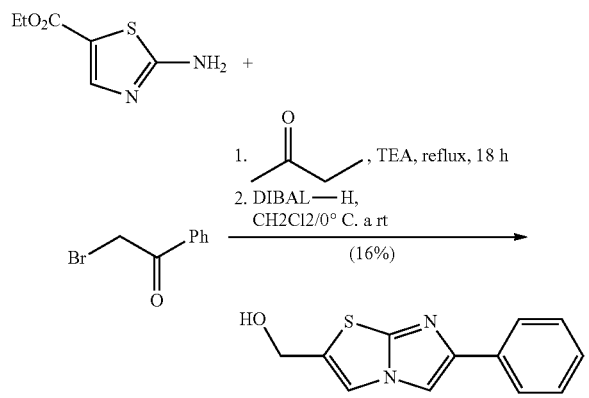

A mixture of ethyl 2-aminothiazole-5-carboxilate (500 mg, 2.9 mmol) and 2-bromoacetophenone (869 mg, 4.35 mmol) in methyl ethyl ketone (50 mL) was refluxed for 1 day under argon atmosphere. The reaction mixture was evaporated to dryness. To a solution of the previous residue in $CH_2Cl_2$ (65 mL), a solution of DIBAL (1.0 M in $CH_2Cl_2$, 12.1 mL, 12.18 mmol) was added. The resulting mixture was stirred for 2 h. The reaction mixture was diluted with water and filtered through Celite®. The layers were separated and the organic phase was dried over $Na_2SO_4$ and evaporated to dryness. The crude product was purified by silica gel column chromatography (EtOAc:MeOH mixtures of increasing polarity as eluent) to afford the desired product (298 mg, 16%).

$^1$H-NMR (DMSO-$d_6$, 400 MHz) δ: 8.15 (s, 1H), 7.83 (m, 3H), 7.37 (m, 2H), 7.23 (tt, J=7.2, 1.4 Hz, 1H), 5.66 (t, J=5.8 Hz, 1H), 4.58 (dd, J=5.6, 1.2 Hz, 2H) ppm.

EI-MS m/z: 230.1 (M).

b) Synthesis of 2-((4-methylpiperazin-1-yl)methyl)-6-phenylimidazo[2,1-b]thiazole maleate

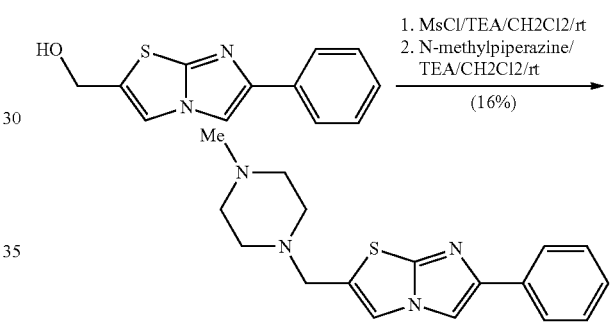

Methanesulfonyl chloride (0.1 mL, 1.29 mmol) and triethylamine (0.18 mL, 1.29 mmol) was added to a suspension of (6-phenylimidazo[2,1-b]thiazol-2-yl)methanol (298 mg, 1.29 mmol) in $CH_2Cl_2$ (4 mL) cooled to 0° C. under argon atmosphere. The resulting mixture was stirred for 15 minutes. The reaction mixture was diluted with brine and extracted with $CH_2Cl_2$. The organic extract was dried with $Na_2SO_4$ and evaporated to dryness. To a solution of the previous residue in $CH_2Cl_2$ (3 mL), N-methylpiperazine (0.17 mL, 1.55 mmol) and triethylamine (0.22 mL, 1.55 mmol) was added. The resulting mixture was stirred overnight. The reaction mixture was diluted with water and extracted with $CH_2Cl_2$. The organic extract was dried with $Na_2SO_4$ and evaporated to dryness. The crude product was purified by silica gel column chromatography (EtOAc/$NH_3$:MeOH mixtures of increasing polarity as eluent) to afford the desired product (13 mg, 16%). The product was converted into the corresponding maleate salt by adding maleic acid (5 mg, 0.04 mmol) in acetone, followed by filtration of the resulting solid and drying under vacuum.

$^1$H-NMR (DMSO-$d_6$, 300 MHz) δ: 8.17 (s, 1H), 7.92 (s, 1H), 7.79 (d, J=7.4 Hz, 2H), 7.38 (t, J=7.8 Hz, 2H), 7.24 (t, J=7.4 Hz, 1H), 6.03 (s, 2H), 3.75 (s, 2H), 3.31 (m, 4H), 3.04 (m, 4H), 2.78 (s, 3H) ppm.

ESI(+)-HRMS: 313.1481 [M+H]$^+$.

Further compounds of the invention are the examples shown in the following table:

| Example | Structure | Method | Name | NMR |
|---|---|---|---|---|
| 6 | ·C₄H₄O₄ | A | 6-(Azepan-1-ylmethyl)-2-phenylimidazo[2,1-b]thiazole maleate | ¹H-NMR (DMSO-d₆, 400 MHz) δ: 8.51 (s, 1H), 7.97 (s, 1H), 7.63 (m, 2H), 7.49 (t, J = 7.6 Hz, 2H), 7.42 (t, J = 7.4 Hz, 1H), 6.06 (s, 2H), 4.34 (s, 2H), 3.37 (m, 4H), 3.19 (m, 2H), 1.79 (m, 3H), 1.60 (m, 3H) ppm. |
| 7 | ·C₄H₄O₄ | A | 6-((4-Methylpiperazin-1-ylmethyl)-2-phenylimidazo[2,1-b]thiazole maleate | ¹H-NMR (DMSO-d₆, 400 MHz) δ: 8.43 (s, 1H), 7.71 (s, 1H), 7.61 (m, 2H), 7.47 (m, 2H), 7.40 (m, 1H), 6.01 (s, 2H), 3.66 (m, 2H), 3.31 (m, 4H), 3.00 (m, 4H), 2.66 (m, 3H) ppm. |
| 8 | ·C₄H₄O₄ | C | 4-(2-((2-Phenylimidazo[2,1-b]thiazol-6-yl)methoxy)ethyl)morpholine maleate | ¹H-NMR (DMSO-d₆, 300 MHz) δ: 8.40 (s, 1H), 7.80 (s, 1H), 7.62 (d, J = 7.8 Hz, 2H), 7.48 (t, J = 7.5 Hz, 2H), 7.39 (m, 1H), 6.04 (s, 2H), 4.52 (s, 2H), 3.76 (m, 6H), 3.23 (m, 3H), 3.15 (m, 3H) ppm. |
| 9 | ·C₄H₄O₄ | C | 6-((2-(Azepan-1-ylethoxy)methyl)-2-phenylimidazo[2,1-b]thiazole maleate | ¹H-NMR (DMSO-d₆, 400 MHz) δ: 9.29 (s, 1H), 8.45 (s, 1H), 7.81 (s, 1H), 7.62 (d, J = 7.6 Hz, 2H), 7.48 (t, J = 7.4 Hz, 2H), 7.39 (t, J = 7.4 Hz, 1H), 6.01 (s, 2H), 4.53 (s, 2H), 3.77 (t, J = 5 Hz, 2H), 3.31 (m, 6H), 1.76 (m, 4H), 1.59 (m, 4H) ppm. |
| 10 | ·C₄H₄O₄ | C | 2-Phenyl-6-((2-(pyrrolidin-1-yl)ethoxy)methyl)imidazo[2,1-b]thiazole maleate | ¹H-NMR (DMSO-d⁶, 400 MHz) δ: 9.49 (s, 1H), 8.44 (s, 1H), 7.81 (s, 1H), 7.62 (m, 2H), 7.47 (m, 2H), 7.38 (m, 1H), 6.03 (s, 2H), 4.54 (s, 2H), 3.73 (m, 2H), 3.49 (m, 2H), 3.31 (m, 2H), 3.02 (m, 2H), 1.96 (m, 2H), 1.87 (m, 2H) ppm. |
| 11 | ·C₄H₄O₄ | A | 6-((4-Methylpiperazin-1-ylmethyl)-2-phenylimidazo[2,1-b][1,3,4]thiadiazole maleate | ¹H-NMR (DMSO-d₆, 400 MHz) δ: 8.16 (s, 1H), 7.92 (m, 2H), 7.60 (m, 3H), 6.07 (s, 2H), 3.66 (m, 2H), 3.31 (m, 4H), 3.04 (m, 4H), 2.72 (m, 3H) ppm. |

| Example | Structure | Method | Name | NMR |
|---|---|---|---|---|
| 12 | C₄H₄O₄ | D | 2-(Azepan-1-ylmethyl)-6-phenylimidazo[2,1-b]thiazole maleate | $^1$H-NMR (DMSO-$d_6$, 400 MHz) δ: 8.28 (s, 1H), 8.13 (s, 1H), 7.82 (d, J = 7.2 Hz, 2H), 7.40 (t, J = 7.6 Hz, 2H), 7.27 (t, J = 7.8 Hz, 1H), 6.09 (s, 2H), 4.55 (m, 2H), 3.31 (m, 4H), 1.76 (m, 4H), 1.61 (m, 4H) ppm. |
| 13 | C₄H₄O₄ | B | 2-(4-Fluorophenyl)-6-((4-methylpiperazin-1-yl)methyl)imidazo[2,1-b]thiazole maleate | $^1$H-NMR (DMSO-$d_6$, 400 MHz) δ: 8.40 (s, 1H), 7.72 (s, 1H), 7.66 (m, 2H), 7.33 (t, J = 8.8 Hz, 2H), 6.12 (s, 2H), 3.69 (m, 2H), 3.30 (m, 6H), 3.06 (m, 2H), 2.69 (m, 3H) ppm. |
| 14 | C₄H₄O₄ | B | 3-(1-((2-Phenylimidazo[2,1-b]thiazol-6-yl)methyl)piperidin-4-yl)phenol maleate | $^1$H-NMR (DMSO-$d_6$, 400 MHz) δ: 9.65 (s, 1H), 9.33 (s, 1H), 8.52 (s, 1H), 8.00 (s, 1H), 7.64 (d, J = 7.6 Hz, 2H), 7.50 (t, J = 7.8 Hz, 1H), 7.43 (m, 1H), 7.10 (t, J = 7.8 Hz, 1H), 6.60 (m, 3H), 6.05 (s, 2H), 4.53 (s, 2H), 4.35 (s, 1H), 3.56 (d, J = 11.6 Hz, 2H), 3.08 (m, 2H), 2.65 (m, 1H), 1.93 (m, 2H), 1.82 (m, 2H) ppm. |

BIOLOGICAL ACTIVITY

Pharmacological Study

Brain membrane preparation and binding assays for the σ1-receptor were performed as described (DeHaven-Hudkins, D. L., L. C. Fleissner, and F. Y. Ford-Rice, 1992, Characterization of the binding of [³H](+)pentazocine to a recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was re-suspended in fresh Tris-HCl buffer (50 mM, pH 7.4) and stored on ice until use.

The radioligand used was [³H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pre-treated glass fiber filterplate (MultiScreen-FC, Millipore), with polyethylenimine 0.1%. The filters were washed two times with 200 μl of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

Some of the results obtained are shown in table (I).

TABLE (I)

| Compound | $K_i$ σ1 (nM) |
|---|---|
| 4 | 168 |
| 6 | 16 |
| 7 | 56 |
| 9 | 40 |
| 10 | 190 |
| 11 | 260 |
| 12 | 100 |
| 13 | 210 |

The invention claimed is:
1. A compound of general formula (I):

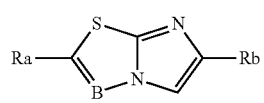

wherein $R_a$ and $R_b$ independently represent a 5 or 6-membered aryl radical optionally substituted by a halogen or a branched or unbranched, saturated or unsaturated, optionally at least mono-substituted, alkyl radical C$_{1-6}$;
a 5 or 6-membered heteroaryl radical having at least one heteroatom selected from N, O or S as ring member, optionally substituted by a halogen or a branched or unbranched, saturated or unsaturated, optionally at least mono-substituted, alkyl radical C$_{1-6}$;
or the following moiety:

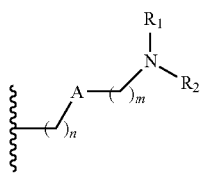

with the proviso that one of R$_a$ and R$_b$ represents this moiety and the other one represents a 5 or 6-membered aryl radical optionally substituted by a halogen or a branched or unbranched, saturated or unsaturated, optionally at least mono-substituted, alkyl radical C$_{1-6}$;
or a 5 or 6-membered heteroaryl radical having at least one heteroatom selected from N, O or S as ring member, optionally substituted by a halogen or a branched or unbranched, saturated or unsaturated, optionally at least mono-substituted, alkyl radical C$_{1-6}$;

A is CH$_2$ or O;

B is CH or N;

R$_1$ and R$_2$ together with the bridging N form a 5 to 7-membered heterocyclic ring which can have at least one additional heteroatom selected from N, O or S and which can be optionally substituted by a branched or unbranched, saturated or unsaturated, alkyl radical C$_{1-6}$ or by an aryl radical optionally substituted by an alkyl C$_{1-6}$, a halogen or an OH group;

n is 0, 1 or 2; and m is 0, 1, 2, 3 or 4;

with the proviso that when A is O, m is different from 0; and with the proviso that when B represents CH and R$_b$ represents a phenyl substituted by a halogen, R$_a$, cannot represent the moiety:

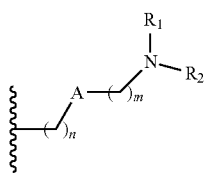

wherein R$_1$ and R$_2$ together with the bridging N form a piperazine, or a pharmaceutically acceptable salt, tautomer, stereoisomer, geometric isomer, prodrug or solvate thereof.

2. The compound according to claim 1, having general formula (Ia):

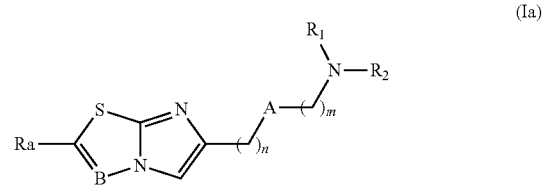

wherein

R$_a$ represents a 5 or 6-membered aryl radical optionally substituted by a halogen or a branched or unbranched, saturated or unsaturated, optionally at least mono-substituted, alkyl radical C$_{1-6}$, or a 5 or 6-membered heteroaryl radical having at least one heteroatom selected from N, O or S as ring member, optionally substituted by a halogen or a branched or unbranched, saturated or unsaturated, optionally at least mono-substituted, alkyl radical C$_{1-6}$;

A is CH$_2$ or O;

B is CH or N;

R$_1$ and R$_2$ together with the bridging N form a 5 to 7-membered heterocyclic ring which can have at least one additional heteroatom selected from N, O or S and which can be optionally substituted by a branched or unbranched, saturated or unsaturated, alkyl radical C$_{1-6}$ or by an aryl radical optionally substituted by an alkyl C$_{1-6}$, a halogen or an OH group;

n is 0, 1 or 2; and m is 0, 1, 2, 3 or 4;

with the proviso that when A is O, m is different from 0.

3. The compound according to claim 1, having general formula (Ib):

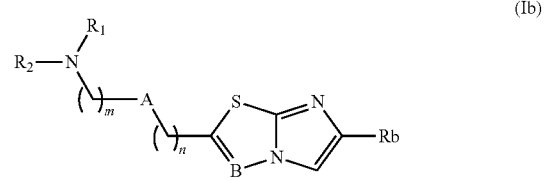

wherein

R$_b$ represents a 5 or 6-membered aryl radical optionally substituted by a halogen or a branched or unbranched, saturated or unsaturated, optionally at least mono-substituted, alkyl radical C$_{1-6}$, or a 5 or 6-membered heteroaryl radical having at least one heteroatom selected from N, O or S as ring member, optionally substituted by a halogen or a branched or unbranched, saturated or unsaturated, optionally at least mono-substituted, alkyl radical C$_{1-6}$;

A is CH$_2$ or O;

B is CH or N;

R$_1$ and R$_2$ together with the bridging N form a 5 to 7-membered heterocyclic ring which can have at least one additional heteroatom selected from N, O or S and which can be optionally substituted by a branched or unbranched, saturated or unsaturated, alkyl radical C$_{1-6}$ or by an aryl radical optionally substituted by an alkyl C$_{1-6}$, a halogen or an OH group;

n is 0, 1 or 2; and m is 0, 1, 2, 3 or 4;

with the proviso that when A is O, m is different from 0; and with the proviso that when B represents CH and $R_b$ represents a phenyl substituted by a halogen $R_1$ and $R_2$ together with the bridging N cannot form a piperazine.

4. The compound according to claim 1, wherein $R_a$ or $R_b$ represents a group selected from:

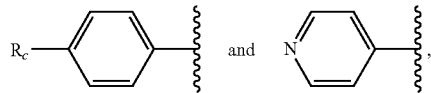

wherein $R_c$, represents H, a $C_{1-6}$ alkyl, or a halogen.

5. The compound according to claim 1, wherein $R_1$ and $R_2$ together with the bridging N form a group selected from:

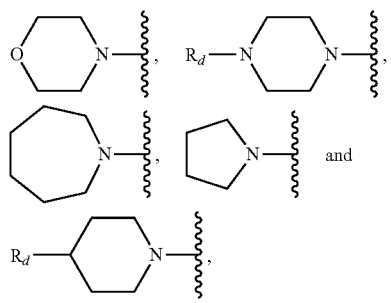

wherein $R_d$ represents a H, a $C_{1-6}$ alkyl or a phenyl group optionally substituted by a $C_{1-6}$ alkyl, a halogen or an —OH group.

6. The compound according to claim 1, wherein A is $CH_2$ and m and n are both 0.

7. The compound according to claim 1, wherein A is O, n is 1 and m is 2.

8. The compound according to claim 1, which is selected from the group consisting of;
[1] 4-((2-phenylimidazo[2,1-b]thiazol-6-yl)methyl)morpholine maleate,
[2] 6-((4-methylpiperazin-1-yl)methyl)-2-(pyridin-4-yl)imidazo[2,1-b]thiazole maleate,
[3] 6-(2-(4-methylpiperazin-1-yl)ethyl)-2-phenylimidazo[2,1-b]thiazole maleate,
[4] 6-((2-(azepan-1-yl)ethoxy)methyl)-2-phenylimidazo[2,1-b][1,3,4]thiadiazole maleate,
[5] 2-((4-methylpiperazin-1-yl)methyl)-6-phenylimidazo[2,1-b]thiazole maleate,
[6] 6-(azepan-1-ylmethyl)-2-phenylimidazo[2,1-b]thiazole maleate,
[7] 6-((4-methylpiperazin-1-methyl)-2-phenylimidazo[2,1-b]thiazole maleate,
[8] 4-(2-((2-phenylimidazo[2,1-b]thiazol-6-yl)methoxy)ethyl)morpholine maleate,
[9] 6-((2-(azepan-1-yl)ethoxy)methyl)-2-phenylimidazo[2,1-b]thiazole maleate,
[10] 2-phenyl-6-((2-(pyrrolidin-1-yl)ethoxy)methyl)imidazo[2,1-b]thiazole maleate,
[11] 6-((4-methylpiperazin-1-yl)methyl)-2-phenylimidazo[2,1-b][1,3,4]thiadiazole maleate,
[12] 2-(azepan-1-ylmethyl)-6-phenylimidazo[2,1-b]thiazole maleate,
[13] 2-(4-fluorophenyl)-6-((4-methylpiperazin-1-yl)methyl)imidazo[2,1-b]thiazole maleate,
[14] 3-(1-((2-phenylimidazo[2,1-b]thiazol-6-yl)methyl)piperidin-4-yl)phenol maleate and pharmaceutically acceptable salts, prodrugs and solvates thereof.

9. A method of treating a sigma receptor mediated disease or condition in a subject in need thereof, comprising administration of an effective amount of a compound according to claim 1 to the subject.

10. The method according to claim 9, wherein the disease or condition is pain.

11. The method according to claim 10, wherein the pain is neuropathic pain, inflammatory pain or other pain conditions involving allodynia and/or hyperalgesia.

12. The method according to claim 11, wherein the neuropathic pain is hyperpathia.

13. The method according to claim 9, wherein the disease is diarrhea; lipoprotein disorders; hyperlipidemia; hypertriglyceridemia; hypercholesterolemia; obesity; migraine; arthritis; hypertension; arrhythmia; ulcer; glaucoma; learning, memory and attention deficits; cognition disorders; neurodegenerative diseases; demyelinating diseases; addiction to drugs and chemical substances; tardive diskinesia, epilepsy, stroke, stress, cancer, psychotic conditions; inflammation or autoimmune diseases.

14. A process for the preparation of a compound of general formula (Iaa) or (Iab):

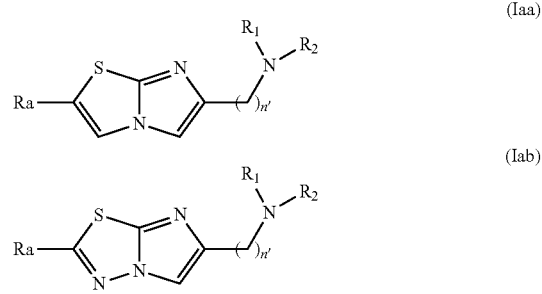

where $R_a$, $R_1$ and $R_2$ have the same meanings as in claim 1 and n' is 1 or 2, the process comprising:
a) the reaction between a compound of general formula (II):

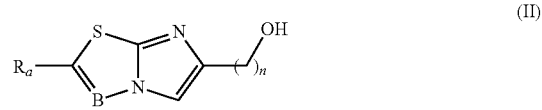

wherein B is CH or N, with a sulphonide halide, and
b) the reaction of the resulting compound with a compound of general formula (III):

the reactions being carried out in the presence of a base in an organic solvent.

15. A process for the preparation of a compound of general formula (Iaa) or (Iab):

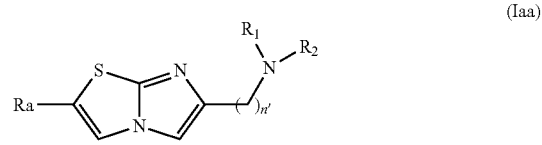

-continued

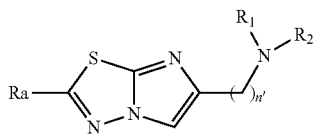
(Iab)

wherein $R_a$, $R_1$ and $R_2$ have the same meanings as in claim 1 and n' is 1 or 2, the process comprising the reaction between a compound of general formula (VII):

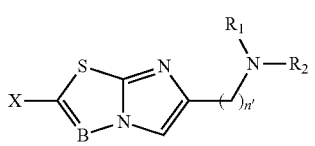
(VII)

wherein X represents a halogen and B represents CH or N, and a compound of general formula (VIII):

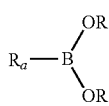
(VIII)

wherein each R group independently represents a hydrogen, a $C_{1-6}$ alkyl or both R groups together with the bridging boron form a boronic cyclic ester, in the presence of a suitable catalyst and a base in an organic solvent.

16. A process for the preparation of a compound of general formula (Iac) or (Iad):

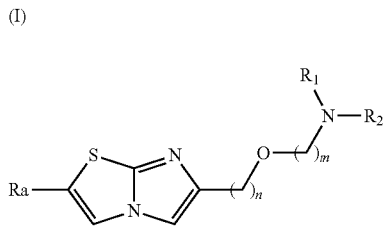
(I)
(Iac)

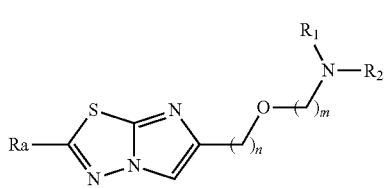
(Iad)

wherein $R_a$, $R_1$, $R_2$, n and m have the same meanings as in claim 1, the process comprising the reaction between a compound of general formula (II):

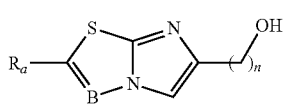
(II)

wherein B is CH or N, and a compound of general formula (XII):

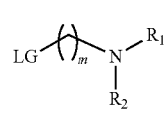
(XII)

wherein LG is a suitable leaving group, in the presence of a base in an organic solvent.

17. A process for the preparation of a compound of general formula (Iba) or (Ibb):

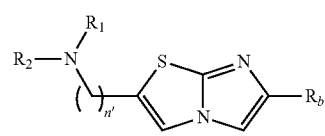
(Iba)

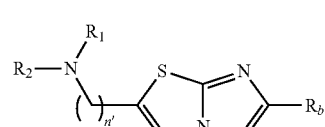
(Ibb)

wherein $R_b$, $R_1$ and $R_2$ have the same meanings as in claim 1 and n' is 1 or 2, the process comprising:
a) reaction between a compound of general formula (XIII):

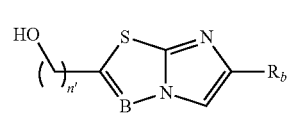
(XIII)

wherein B is CH or N, with a sulphonide halide and
b) reaction of the resulting compound with a compound of general formula (III):

$R_1R_2NH$ (III)

the reactions being carried out in the presence of a base in an organic solvent.

18. A pharmaceutical composition comprising a compound according to claim 1, and at least a pharmaceutically acceptable carrier, additive, adjuvant or vehicle.

19. The method of claim 11, wherein the allodynia is mechanical allodynia or thermal allodynia.

20. The method of claim 13, wherein the disease is addiction to cocaine, addiction to amphetamines, addiction to ethanol or addiction to nicotine.

21. The method of claim 13, wherein the psychotic condition is depression, anxiety or schizophrenia.

22. The process of claim 15, wherein the R groups together with the bridging boron form a boronic acid pinacol ester.

23. The process of claim 16, wherein LG is a halogen.

24. A compound of general formula (I):

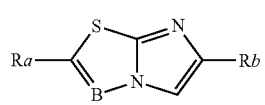
(I)

wherein
$R_a$ and $R_b$ independently represent a group selected from:

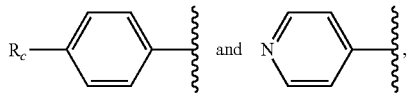

wherein $R_c$ represents H, a $C_{1-6}$ alkyl, a halogen or an —OR' group wherein R' represents a linear or branched $C_{1-6}$-alkyl group; or the following moiety:

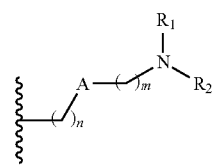

with the proviso that one of $R_a$ and $R_b$ represents this moiety and the other one represents a group selected from:

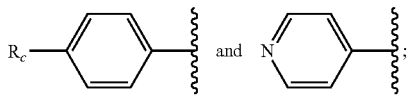

A is $CH_2$ or O;
B is CH or N;
$R_1$ and $R_2$ together with the bridging N form a 5 to 7-membered heterocyclic ring which can have at least one additional heteroatom selected from N, O or S and which can be optionally substituted by a branched or unbranched, saturated or unsaturated, alkyl radical $C_{1-6}$ or by an aryl radical optionally substituted by an alkyl $C_{1-6}$, a halogen or an OH group;
n is 0, 1 or 2; and
m is 0, 1, 2, 3 or 4;
with the proviso that when A is O, m is different from 0; and
with the proviso that when B represents CH and $R_b$ represents a phenyl substituted by a halogen, $R_a$ cannot represent the moiety:

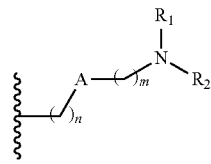

wherein $R_1$ and $R_2$ together with the bridging N form a piperazine,
or a pharmaceutically acceptable salt, tautomer, stereoisomer, geometric isomer, prodrug or solvate thereof.

* * * * *

UNITED STATES PATENT AND TRADEMARK OFFICE
CERTIFICATE OF CORRECTION

PATENT NO. : 9,617,281 B2
APPLICATION NO. : 14/412257
DATED : April 11, 2017
INVENTOR(S) : María de las Ermitas Alcalde-Pais et al.

It is certified that error appears in the above-identified patent and that said Letters Patent is hereby corrected as shown below:

On the Title Page

Column 1, item (73) Assignee:
"LABORATORIES"
Should read:
--LABORTORIOS--.

In the Claims

Column 34, Line 45, Claim 14, Formula (II):

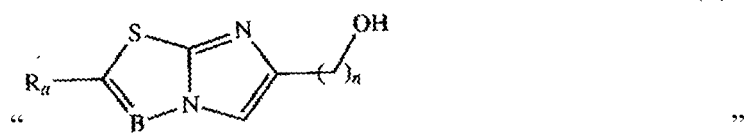

Should read:

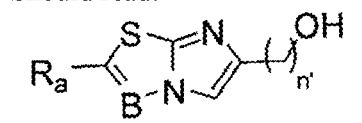

--.

Signed and Sealed this
Tenth Day of July, 2018

Andrei Iancu
*Director of the United States Patent and Trademark Office*